(12) United States Patent
Dong et al.

(10) Patent No.: US 11,123,723 B2
(45) Date of Patent: Sep. 21, 2021

(54) OXIDATIVE DEHYDROXYMETHYLATION OF ALCOHOLS TO PRODUCE OLEFINS

(71) Applicant: The Regents of the University of California, Oakland, CA (US)

(72) Inventors: Vy M. Dong, Irvine, CA (US); Faben A. Cruz, Irvine, CA (US); Xuesong Wu, Irvine, CA (US); Steven M. Bischof, Humble, TX (US); Stephen Karl Murphy, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 312 days.

(21) Appl. No.: 16/284,076

(22) Filed: Feb. 25, 2019

(65) Prior Publication Data

US 2019/0262819 A1    Aug. 29, 2019

Related U.S. Application Data

(60) Provisional application No. 62/634,986, filed on Feb. 26, 2018.

(51) Int. Cl.

| | | |
|---|---|---|
| *C07C 1/24* | (2006.01) | |
| *B01J 31/00* | (2006.01) | |
| *B01J 31/24* | (2006.01) | |
| *B01J 31/02* | (2006.01) | |
| *B01J 31/22* | (2006.01) | |
| *C07C 1/207* | (2006.01) | |
| *C07C 11/02* | (2006.01) | |

(52) U.S. Cl.
CPC ....... *B01J 31/2457* (2013.01); *B01J 31/0205* (2013.01); *B01J 31/0247* (2013.01); *B01J 31/2295* (2013.01); *C07C 1/2076* (2013.01); *C07C 1/24* (2013.01); *B01J 2231/763* (2013.01); *B01J 2531/822* (2013.01); *C07C 11/02* (2013.01); *C07C 2531/04* (2013.01); *C07C 2531/22* (2013.01); *C07C 2531/24* (2013.01)

(58) Field of Classification Search
CPC ....... C07C 1/24; C07C 1/2076; B01J 31/2457
See application file for complete search history.

(56) References Cited

U.S. PATENT DOCUMENTS

| | | |
|---|---|---|
| 3,078,313 A | 2/1963 | Brown |
| 3,358,034 A | 12/1967 | Brown |
| 3,439,046 A | 4/1969 | Brown |
| 3,582,270 A | 6/1971 | Harkema |
| 4,272,444 A | 6/1981 | McCombs et al. |
| 5,123,494 A | 7/1992 | Gilheany et al. |
| 8,765,984 B2 | 7/2014 | Upshaw |
| 9,115,069 B2 | 8/2015 | Papp et al. |
| 10,183,899 B2 | 1/2019 | Bischof |
| 10,435,334 B2 | 10/2019 | Bischof |
| 2002/0193650 A1 | 12/2002 | Goze et al. |
| 2007/0004939 A1 | 1/2007 | Volland et al. |
| 2011/0160495 A1 | 6/2011 | Hasling et al. |
| 2013/0274482 A1 | 10/2013 | Schrock et al. |
| 2019/0144356 A1 | 5/2019 | Bischof |
| 2019/0263729 A1 | 8/2019 | Bischof et al. |

FOREIGN PATENT DOCUMENTS

| | | |
|---|---|---|
| CA | 1048533 | 2/1979 |
| EP | 1 892 280 | 2/2008 |
| WO | WO 89/06225 | 7/1989 |
| WO | WO 2001/00546 | 1/2001 |
| WO | WO 2001/05735 | 1/2001 |
| WO | WO 2014/088800 | 6/2014 |
| WO | WO 2015/094813 | 6/2015 |

OTHER PUBLICATIONS

Brown et al., "A Stereospecific cis Hydration of the Double Bond in Cyclic Derivatives," Journal of the American Chemical Society, (1959), 81:247.
Brown et al., "Communications—Selective Conversion of Olefins into Organoboranes Through Competitive Hydroboration, Isomerization and Displacement Reactions," Journal of Organic Chemistry, (1957), 22 (9):1137.
Chatterjee et al., "A General Model for Selectivity in Olefin Cross Metathesis," J. Am. Chem. Soc. (2003), vol. 125, pp. 11360-11370.
Chatterjee et al., "A General Model for Selectivity in Olefin Cross Metathesis," J. Am. Chem. Soc. (2003), Supporting Info., pp. S1-S27.
Haymore et al., "Regioselectivity in Hydroformylation of Linear and Branched Octenes Using $HCo(CO)_4$," Annals NY Academy of Sciences (1983), vol. 415, pp. 159-175.
Jacobsen et al., "Asymmetric dihydroxylation via ligand-accelerated catalysis," J. Am. Chem. Soc. (1988), 110 (6):1968-1970.
Kabalka et al., "Mild and convenient oxidation procedure for the conversion of organoboranes to the corresponding alcohols," J. Org. Chem. (1975), 40, 1776-1779.
Keim, "Oligomerization of Ethylene to a-Olefins: Discovery and Development of the Shell Higher Olefin Process (SHOP)," Angew. Chem. Int. Ed. (2013), vol. 52, pp. 12492-12496.
Kolb et al., "Catalytic Asymmetric Dihydroxylation," Chem. Rev. (1994) 94 (8):2483-2547.
Kreis et al., "A General and Convenient Method for the Rhodium-Catalyzed Decarbonylation of Aldehydes," ChemInform, Wiley-VCH Verlag GmbH & Co. KGAA, DE (2007), vol. 38, No. 6, 1 page.
Landis, "Construction and deconstruction of aldehydes by transfer hydroformylation," Science (2015), vol. 347, No. 6217, pp. 29-30.
Luo et al., "Mechanism of Rhodium-Catalyzed Formyl Activation: A Computational Study," J. Org. Chem., (2016), 81, 2320-2326.

(Continued)

*Primary Examiner* — Sikarl A Witherspoon
(74) *Attorney, Agent, or Firm* — Merchant & Gould P.C.

(57) ABSTRACT

Catalyst compositions for the conversion of aldehyde compounds and primary alcohol compounds to olefins are disclosed herein. Reactions include oxidative dehydroxymethylation processes and oxidative dehydroformylation methods, which are beneficially conducted in the presence of a sacrificial acceptor of $H_2$ gas, such as N,N-dimethylacrylamide.

27 Claims, No Drawings

(56) References Cited

OTHER PUBLICATIONS

Malcho et al., "*Ionic liquids as recyclable and separable reaction media in Rh-catalyzed decarbonylation of aromatic and aliphatic aldehydes,*" RSC Adv. (2014), vol. 4, No. 102, pp. 58151-58155.

Murphy et al., "*Rh-catalyzed C—C bond cleavage by transfer hydroformylation,*" Science (2014), Supporting Info., vol. 347, Issue 56, pp. S1-S71.

Murphy et al., "*Rh-catalyzed C—C bond cleavage by transfer hydroformylation,*" Science (2015), vol. 347, Issue 6217, p. 56-60.

Ohno et al., "*Organic Synthesis by Means of Noble Metal Compounds. XXXV. Novel Decarbonylation Reactions of Aldehydes and Acyl Halides Using Rhodium Complexes,*" Journal of the American Chemical Society (1968), vol. 90, No. 1, pp. 99-107.

Olsen et al., "*Iridium-Catalyzed Dehydrogenative Decarbonylation of Primary Alcohols with the Liberation of Syngas,*" Chem. Eur. J. (2012), vol. 18, No. 50, pp. 16023-16029.

Pandey et al., "*Terminal Olefins from Aldehydes through Enol Triflate Reduction,*" J. Org. Chem. (2007), vol. 72, pp. 7769-7770.

Selent et al., "*New Phosphorus Ligands for the Rhodium-Catalyzed Isomerization/Hydroformylation of Internal Octenes,*" Angew. Chem. Int. Ed. (2001), vol. 40, No. 9, pp. 1696-1698.

Thomas et al., "*Highly Selective Ruthenium Metathesis Catalysts for Ethenolysis,*" J. Am. Chem. Soc. (2011), vol. 133, pp. 7490-7496.

Thomas et al., "*Highly Selective Ruthenium Metathesis Catalysts for Ethenolysis,*" J. Am. Chem. Soc. (2011), Supporting Info, pp. S1-S32.

VanRheenen et al., "*An improved catalytic $OsO_4$ oxidation of olefins to cis-1, 2-glycols using tertiary amine oxides as the oxidant,*" Tetrahedron Lett. (1976) 17 (23):1973-1976.

Wu et al., "*Tandem Catalysis: Transforming Alcohols to Alkenes by Oxidative Dehydroxymethylation,*" J. Am. Chem. Soc. (2018), vol. 140, No. 32, pp. 10126-10130.

Zweifel et al., "*Hydroboration. XIII. The hydroboration of dienes with disiamylborane. A convenient procedure for the conversion of selected dienes into unsaturated alcohols,*" J. Am. Chem. Soc. (1962) 84, 190-95.

International Search Report and the Written Opinion of the International Searching Authority in PCT/US2019/019370 dated Jun. 3, 2019, 21 pages.

OXIDATIVE DEHYDROXYMETHYLATION OF ALCOHOLS TO PRODUCE OLEFINS

REFERENCE TO RELATED APPLICATION

This application claims the benefit of U.S. Provisional Patent Application No. 62/634,986, filed on Feb. 26, 2018, the disclosure of which is incorporated herein by reference in its entirety.

STATEMENT REGARDING FEDERALLY SPONSORED RESEARCH OR DEVELOPMENT

This invention was made with Government support under Grant No. GM105938, awarded by the National Institutes of Health. The Government has certain rights in this invention.

BACKGROUND OF THE INVENTION

Methods of synthesizing olefins are very important due to the high occurrence of olefins in many useful materials, and their versatile reactivity. It would be beneficial to develop new transformation reactions that can convert aldehyde compounds and alcohol compounds directly into olefinic compounds. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to catalyst compositions, oxidative dehydroxymethylation processes, and oxidative dehydroformylation methods. Catalyst compositions of the present invention can promote oxidative reaction pathways to produce α-olefins from alcohols and aldehydes in excellent yield, and with unexpected selectivity over byproducts such as alkanes and internal olefins.

Catalyst compositions described herein can comprise a Group VIII metal compound, a heteroatomic ligand compound, and a Bronsted acid compound. These catalyst compositions can further comprise an acceptor (e.g., N,N-dimethylacrylamide) capable of accepting a molecule of $H_2$, for instance during oxidative dehydroxymethylation and oxidative dehydroformylation reaction steps.

The present invention also encompasses oxidative dehydroxymethylation processes, and such processes can comprise contacting any of the catalyst compositions disclosed herein with a substituted or unsubstituted $C_n$ primary alcohol compound to form a reaction mixture comprising a substituted or unsubstituted $C_{(n-1)}$ olefin. The integer, n, can range from 3 to 36. In circumstances where the primary alcohol compound is a 1,2-diol, the process can form a $C_{(n-2)}$ olefin, and n can range from 4 to 36. Also contemplated herein are oxidative dehydroformylation methods, and such methods can comprise contacting any catalyst composition disclosed herein with a substituted or unsubstituted $C_n$ aldehyde compound to form a reaction mixture comprising a substituted or unsubstituted $C_{(n-1)}$ olefin. In this method, n is an integer that can range from 3 to 36. The processes and methods disclosed herein advantageously can produce α-olefin products from primary alcohol compounds and/or aldehyde compounds in yields in excess of 90%.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein can be combined to describe inventive designs, compositions, processes, or methods consistent with the present disclosure.

While compositions and processes/methods are described herein in terms of "comprising" various components or steps, the compositions and processes/methods can also "consist essentially of" or "consist of" the various components or steps, unless stated otherwise. For example, a catalyst composition consistent with aspects of the present invention can comprise; alternatively, can consist essentially of; or alternatively, can consist of; a Group VIII metal compound, a heteroatomic ligand compound, a Bronsted acid compound, and optionally, an acceptor.

The terms "a," "an," and "the" are intended to include plural alternatives, e.g., at least one, unless otherwise specified. For instance, the disclosure of "a Group VIII metal compound" or "a heteroatomic ligand compound" is meant to encompass one, or combinations of more than one, Group VIII metal compound or heteroatomic ligand compound, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; and a general reference to cyclododecatriene includes all isomeric forms (e.g., trans,trans,cis-1,5,9-cyclododecatriene, and trans,trans,trans-1,5,9-cyclododecatriene, among other dodecatrienes).

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contact product," "contacting," and the like, are used herein to describe compositions and processes/methods wherein the components are contacted or combined together in any order, in any manner, and for any length of time, unless otherwise specified. For example, the components can be contacted by blending or mixing. Further, unless otherwise specified, the contacting of any component can occur in the presence or absence of any other component of the compositions and processes/methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted or combined in some other manner. Hence, "contacting" two or more components can result in a mixture, a reaction product, a reaction mixture, etc.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the Group VIII metal compound, the heteroatomic ligand compound, the Bronsted acid compound, and the acceptor, after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

As utilized herein, the term "solvent" applies to a material which can dissolve a compound, or a material which can dilute the components of a reaction. As such, the term "solvent" can encompass materials which can act as a diluent, unless expressly stated otherwise.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION

The present invention is directed generally to catalyst compositions, processes for using the catalyst compositions in oxidative dehydroxymethylation reactions, and methods for using the catalyst compositions in oxidative dehydroformylation reactions. More particularly, synthesis techniques for the conversion of alcohols or aldehydes to olefins are disclosed herein. Beneficially, the disclosed processes and methods can selectively produce α-olefins, while minimizing byproduct alkanes and internal olefins.

Catalyst Compositions

Disclosed herein are catalyst compositions useful in oxidative dehydroxymethylation processes in which primary alcohol compounds can be converted to olefins, and oxidative dehydroformylation methods in which aldehyde compounds can be converted to olefins, as described below. Generally, catalyst compositions of the present invention can comprise (i) a Group VIII metal compound, (ii) a heteroatomic ligand compound, and (iii) a Bronsted acid compound. Optionally, such catalyst compositions further comprise an acceptor. Additionally, catalyst compositions contemplated herein can further comprise a solvent, if desired.

Generally, the Group VIII metal compound can be any compound comprising a Group VIII metal. In certain aspects, the Group VIII metal compound can be a rhodium compound, a cobalt compound, or an iridium compound. More than one Group VIII metal compound can be used in the catalyst composition. In certain aspects, the Group VIII metal compound can be a metal precursor having labile ligands that can be readily displaced by the heteroatomic ligand, Bronsted acid, acceptor, solvent, or any combination thereof, in order to provide access to the metal of the Group VIII metal compound during the reaction. In a particular aspect of this invention, the Group VIII metal compound can be a rhodium compound, a non-limiting example of which is a rhodium precursor compound such as [Rh(cod)OMe]2.

While not wishing to be bound by theory, it is believed that the Group VIII metal of the metal compound can serve as an active site for catalyzing reactions between the other catalyst composition components and reagents to form any number of coordination complexes that can exist in equilibrium, and establish the molecular framework for conducting the processes and methods disclosed herein. Thus, the catalyst compositions described herein are intended to encompass both the initial combination of components disclosed herein, and all coordination complexes or other contact products formed by contacting the components of the catalyst composition. In certain aspects, the catalyst composition can further comprise a solvent, which can allow the other catalyst components to interact and form active coordination complexes and contact products. In some aspects, the solvent can be a hydrophobic solvent capable of dissolving each of the components of the catalyst composition. Suitable solvents for use in the catalyst compositions disclosed herein can include aromatic solvents, aliphatic solvents, ethers, saturated hydrocarbons, unsaturated hydrocarbons, or any combination thereof. Non-limiting examples of suitable solvents include toluene, benzene, xylene, and anisole. It is conceivable that in certain aspects, the solvent can be the same as the acceptor, discussed hereinbelow.

In some aspects, the heteroatomic ligand compound can be any compound that is capable of forming a coordination complex with the Group VIII metal compounds disclosed herein. Accordingly, the donor groups of the heteroatomic ligand compound are not limited to any particular type or combination of donor group. In certain aspects, the heteroatomic ligand compound can comprise one or more neutral donor groups; alternatively, an amine donor group, a phosphine donor group, an ether donor group, a sulfide donor group, or any combination thereof; alternatively, a phosphine donor group; or alternatively, multiple phosphine donor groups.

Moreover, it can be advantageous for the heteroatomic ligand compound to form a strong coordination with the Group VIII metal of the metal compound, relative to other catalyst composition components. In this manner, the heteroatomic ligand can remain coordinated to the metal throughout the reaction despite the presence of other coordinating groups in the reaction mixture. As will be apparent to those of skill in the art, multidentate ligands often can bind more strongly than monodentate ligands. Thus, in certain aspects, the heteroatomic ligand compound can comprise one donor group, or more than one donor group, e.g., 2 donor groups, 3 donor groups, or 4 donor groups, wherein the heteroatomic ligand compound can have a denticity of 2, 3, or 4, respectively. Suitable heteroatomic ligand compounds contemplated herein also can be selected based on their solubility and ability to impart solubility to coordination complexes formed within the catalyst composition and/or during the reaction. Given these considerations, the heteroatomic ligand compound contemplated herein advantageously can comprise neutral donor groups and/or hydrocarbyl substituents (e.g., aromatic, bulky alkyl groups) to impart solubility in hydrophobic solvents. Generally, phosphine donor groups can coordinate strongly to the metal of the Group VIII metal compound and accommodate bulky hydrocarbyl group substituents. Accordingly, the heteroatomic ligand compound can be a bidentate aromatic phosphine compound. An example of a suitable heteroatomic ligand compound is Xantphos, which is shown below (Ph is phenyl).

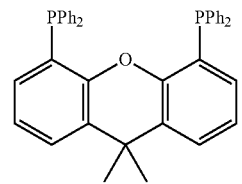

Based on the relative coordination strength of certain heteroatomic ligand compounds, the molar ratio (metal:ligand) of the Group VIII metal compound to the heteroatomic ligand compound ultimately can dictate the amount and configuration of available metal coordination sites at which the less strongly coordinating components of the catalyst composition may coordinate to the metal and react with reagents and reaction intermediates. While not being limited thereto, the molar ratio (metal:ligand) of the Group VIII metal compound to the heteroatomic ligand compound often can be in a range from about 5:1 to about 1:5. Other suitable non-limiting ranges for the molar ratio of the Group VIII metal compound to the heteroatomic ligand compound can include the following ranges: from about 4:1 to about 1:4, from about 3:1 to about 1:3, from about 2:1 to about 1:2, from about 1.1:1 to about 3:1, or from about 1:1 to about 2:1. In some aspects, the molar ratio can be equal to about 1:1 (stoichiometric based on the molar equivalents of the compounds).

As one of skill in the art will appreciate, the amount of heteroatomic ligand compound required to fill a certain number of coordinating sites on the Group VIII metal compound can depend on its denticity. For instance, a bidentate heteroatomic ligand compound (having two donor groups) requires half of the molar equivalent of a monodentate heteroatomic ligand compound to occupy the same amount of metal coordination sites. Moreover, the Group VIII metal compound can be a dimeric metal precursor comprising more than one Group VIII metal atom, such as [Rh(cod)OMe]$_2$. Accordingly, the molar ratio (metal:donor) of the Group VIII metal to the donor groups of the heteroatomic ligand compound also can be any range listed above, or alternatively, equal to about 1:1 (stoichiometric). Other appropriate ranges for the molar ratio of the Group VIII metal compound to the heteroatomic ligand compound, and the Group VIII metal to the donor groups of the heteroatomic ligand compound are readily apparent from this disclosure.

Bronsted acid compounds contemplated herein generally can be any compound having a functional group able to donate a proton, and also capable of coordinating to the metal of the Group VIII metal compound. Thus, the Bronsted acid compound can be capable of functioning as a proton shuttle between reagents and other components of the catalyst composition, at a Group VIII metal coordination site. In certain aspects, the Bronsted acid compound can coordinate to the metal compound with two donor groups such that the Bronsted acid compound can alternately adopt a monodentate or bidentate coordination to the metal, dependent on the relative coordination strength of other donor groups present in the reaction mixture and coordinated to the metal compound. Thus, in certain aspects, the Bronsted acid compound can comprise a carboxylic group. As stated above for other components, the Bronsted acid compound can be chosen based on its solubility in a hydrophobic solvent, such that substituted or unsubstituted aromatic compounds can be advantageous. Accordingly, in certain aspects, the Bronsted acid compound can be a substituted or unsubstituted benzoic acid, e.g., 3-methoxybenzoic acid.

The amount of the Bronsted acid compound in the catalyst composition is not limited to any particular amount. While not being limited thereto, the molar ratio of the heteroatomic ligand compound to the Bronsted acid compound often can be in a range from about 5:1 to about 1:5. Other suitable non-limiting ranges can include the following ranges: from about 4:1 to about 1:4, from about 3:1 to about 1:3, from about 2:1 to about 1:2, from about 1.1:1 to about 3:1, or from about 1:1 to about 2:1. In some aspects, the molar ratio can be equal to about 1:1 (stoichiometric).

Suitable acceptors for the catalyst compositions and processes/methods contemplated herein generally can comprise any compound capable of coordinating to the metal and able to be reduced with an equivalent of H$_2$. In theory, the acceptor can include any number of compounds containing an alkene group, an aromatic group, a ketone group, or practically any π-bonded group within its structure. For example, alkenes and α,β-unsaturated compounds have demonstrated excellent performance as acceptors in the catalyst compositions described herein. In certain aspects, the acceptor can comprise a strained alkene, such as norbornene, norbornadiene, or both. In other aspects, the acceptor can comprise an α,β-unsaturated ketone, an α,β-unsaturated amide, and/or an α,β-unsaturated thioester. Examples of suitable acceptor compounds can include methyl vinyl ketone, acrylonitrile, ethyl acrylate, t-butyl acrylate, acrylamide, dimethylacrylamide, or any combination thereof.

Due to the sacrificial role of the acceptor in the catalyst composition, the acceptor may be present in a large molar excess relative to other catalyst components, and depend on the amount of reactants to be consumed in a reaction employing the catalyst composition rather than, for instance, the amount of the Group VIII metal compound present. Generally, however, a molar ratio of the metal compound to the acceptor can be in a range from about 1:1000 to about 1:1, from about 1:500 to about 1:1, from about 1:200 to about 1:1, from about 1:200 to about 1:2, from about 1:200 to about 1:5, or from about 1:100 to about 1:10.

As stated above, it is believed that coordination complexes resulting from specific combinations of catalyst components described above can contribute to the reactivity of the catalyst composition. It will be apparent to one of skill in the art that the steric and electronic properties of the resulting coordination complexes, particularly with respect to the metal of the Group VIII metal compound, can be particularly important. Accordingly, while the selection of individual components of the catalyst compositions may not be particularly limited, certain combinations can result in exceptional and unexpected performance, as demonstrated by the examples that follow.

Oxidative Dehydroxymethylation Processes

Oxidative dehydroxymethylation processes for the conversion of primary alcohol compounds to olefins can comprise contacting any catalyst composition described herein with a substituted or unsubstituted C$_n$ primary alcohol compound to form a reaction mixture comprising a substituted or unsubstituted C$_{(n-1)}$ olefin. In these processes, n can be an integer from 3 to 36. The reaction below shows a representative example of an oxidative dehydroxymethylation process to form propylene from 1-butanol.

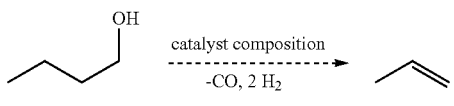

Additionally or alternatively, certain aspects of the oxidative dehydroxymethylation processes described herein can comprise contacting any catalyst composition described herein with a substituted or unsubstituted C$_n$ primary alcohol compound to form a reaction mixture comprising a substituted or unsubstituted C$_{(n-2)}$ olefin. In such aspects, n can be an integer from 4 to 36, and the primary alcohol compound can be a 1,2-diol. The reaction below shows a representative example of the oxidative dehydroxymethylation process to form propylene from 1,2-pentanediol.

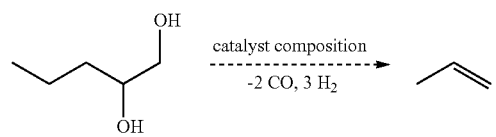

In general, the C$_n$ primary alcohol compound can be any substituted or unsubstituted C$_3$-C$_{36}$ primary alcohol compound. In certain aspects, the primary alcohol compound can be a C$_3$-C$_{36}$ primary alcohol compound, a C$_3$-C$_{24}$ primary alcohol compound, a C$_3$-C$_{18}$ primary alcohol compound, a C$_3$-C$_{12}$ primary alcohol compound, a C$_3$-C$_{10}$ primary alcohol compound, or a C$_3$-C$_8$ primary alcohol compound. In certain processes contemplated herein, the primary alcohol compound can be a C$_3$ primary alcohol compound, a C$_4$ primary alcohol compound, a C$_5$ primary alcohol compound, a C$_6$ primary alcohol compound, a C$_7$ primary alcohol compound, a C$_8$ primary alcohol compound, a C$_9$ primary alcohol compound, a C$_{10}$ primary alcohol compound, a $C_{11}$ primary alcohol compound, a $C_{12}$ primary alcohol compound, a $C_{13}$ primary alcohol compound, a $C_{14}$ primary alcohol compound, a $C_{15}$ primary alcohol compound, a $C_{16}$ primary alcohol compound, a $C_{17}$ primary alcohol compound, or a $C_{18}$ primary alcohol compound. Combinations of two or more primary alcohol compounds can be used in the processes described herein.

Additionally, the primary alcohol compound can be a linear or branched primary alcohol compound, a saturated or unsaturated primary alcohol compound, or a cyclic primary alcohol compound. In some aspects, the primary alcohol compound can be 1-propanol, 1-butanol, 1-hexanol, 1-heptanol, 1-octanol, 2-ethyl-1-hexanol, 1-decanol, 1-undecanol, a 1-dodecanol, 2-ethyl-1-decanol, and mixtures thereof. As stated above, the primary alcohol compound also can be a 1,2-diol; such compounds can be similarly substituted or unsubstituted, linear or branched, saturated or unsaturated, or cyclic, as described herein.

Optionally, the primary alcohol compounds contemplated herein can be substituted with one or more substituents independently selected from a $C_1$-$C_{18}$ hydrocarboxy group, a $C_1$-$C_{18}$ hydrocarbylaminyl group, a secondary hydroxyl group, a tertiary hydroxyl group, a halogen, a cyano group, or a thiol group.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to about 18 carbon atoms (e.g., $C_1$ to $C_{18}$, $C_1$ to $C_{10}$, or $C_1$ to $C_8$ hydrocarboxy groups). Illustrative and non-limiting examples of hydrocarboxy groups can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be a substituent of the primary alcohol compound at any suitable position can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups can comprise up to about 18 carbon atoms (e.g., $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group can be, for instance, a methylaminyl group (—NHCH$_3$), an ethylaminyl group (—NHCH$_2$CH$_3$), an n-propylaminyl group (—NHCH$_2$CH$_2$CH$_3$), an iso-propylaminyl group (—NHCH(CH$_3$)$_2$), an n-butylaminyl group (—NHCH$_2$CH$_2$CH$_2$CH$_3$), a t-butylaminyl group (—NHC(CH$_3$)$_3$), an n-pentylaminyl group (—NHCH$_2$CH$_2$CH$_2$CH$_2$CH$_3$), a neo-pentylaminyl group (—NHCH$_2$C(CH$_3$)$_3$), a phenylaminyl group (—NHC$_6$H$_5$), a tolylaminyl group (—NHC$_6$H$_4$CH$_3$), or a xylylaminyl group (—NHC$_6$H$_3$(CH$_3$)$_2$); alternatively, a methylaminyl group; alternatively, an ethylaminyl group; alternatively, a propylaminyl group; or alternatively, a phenylaminyl group. In other aspects, the hydrocarbylaminyl group which can be, for instance, a dimethylaminyl group (—N(CH$_3$)$_2$), a diethylaminyl group (—N(CH$_2$CH$_3$)$_2$), a di-n-propylaminyl group (—N(CH$_2$CH$_2$CH$_3$)$_2$), a di-iso-propylaminyl group (—N(CH(CH$_3$)$_2$)$_2$), a di-n-butylaminyl group (—N(CH$_2$CH$_2$CH$_2$CH$_3$)$_2$), a di-t-butylaminyl group (—N(C(CH$_3$)$_3$)$_2$), a di-n-pentylaminyl group (—N(CH$_2$CH$_2$CH$_2$CH$_2$CH$_3$)$_2$), a di-neo-pentylaminyl group (—N(CH$_2$C(CH$_3$)$_3$)$_2$), a di-phenylaminyl group (—N(C$_6$H$_5$)$_2$), a di-tolylaminyl group (—N(C$_6$H$_4$CH$_3$)$_2$), or a di-xylylaminyl group (—N(C$_6$H$_3$(CH$_3$)$_2$)$_2$); alternatively, a dimethylaminyl group; alternatively, a di-ethylaminyl group; alternatively, a di-n-propylaminyl group; or alternatively, a di-phenylaminyl group.

In certain aspects, one or more substituents of the primary alcohol compound may comprise one or more protecting groups commonly used to ensure certain functional groups are not affected during a particular reaction, or series of reactions. For instance, the primary alcohol compound can comprise a hydroxyl-protecting group, a carboxyl-protecting group, a ketone-protecting group, an amino protecting group, a mercapto-protecting group, or any combination thereof. Certain aspects of the processes disclosed herein are capable of converting a primary alcohol compound into an olefin under conditions that do not affect any hydroxyl-protecting group, carboxyl-protecting group, ketone-protecting group, amino protecting group, and/or mercapto-protecting group present within the primary alcohol compound.

In other aspects, one or more substituents of the primary alcohol compound may comprise one or more unprotected hydroxyl groups, one or more unprotected carboxyl groups, one or more unprotected ketone groups, one or more unprotected amino groups, and/or one or more unprotected mercapto groups. In some aspects, unprotected groups can have no significant effect on the rate of reaction, amount of olefin produced, or selectivity of the reaction to produce α-olefins.

Olefins produced by the processes disclosed herein can comprise substituted or unsubstituted olefins, linear or branched olefins, saturated or unsaturated olefins, and cyclic olefins, analogous to the primary alcohol compounds described above. In certain aspects, rearrangements can occur depending on the structure of the primary alcohol compound and reaction conditions resulting in an internal olefin; however, the olefins produced by the processes disclosed herein typically can be α-olefins. Accordingly, aspects in which the primary alcohol compound is an unsubstituted linear primary alcohol (e.g., 1-undecanol, 1-butanol) can produce a normal $C_{(n-1)}$ α-olefin (e.g., 1-decene, propylene, respectively). Similarly, processes of the present invention in which the primary alcohol compound is a 1,2-diol can produce a $C_{(n-2)}$ olefin analogous to the primary alcohol compounds, as described above. Thus, contacting the catalyst composition with 1,2-undecanediol can produce 1-nonene. Similarly, contacting the catalyst composition with 1,2-butanediol can produce ethylene.

Molar yields of the olefin products are determined based on the moles of the primary alcohol. Where the yields of olefins are determined by analysis of the crude reaction mixture, an internal standard can be used to correlate the molar concentration of the standard to the olefin product (or byproduct) in question. In certain aspects, the presence of an acceptor in the catalyst composition can unexpectedly and drastically improve the yield of the desired olefin product (e.g., α-olefin), while minimizing byproducts such as internal olefins. Generally, the molar yield of the $C_{(n-1)}$ olefin produced by the disclosed processes can be at least about 10%, at least about 20%, at least about 30%, at least about 40%, at least about 50%, at least about 60%, at least about 70%, at least about 80%, at least about 90%, at least about 95%, at least about 98%, or at least about 99%. The molar yield is based on the initial amount (moles) of the primary alcohol compound.

Moreover, selectivity for the desired olefin product can be drastically improved by use of the processes disclosed herein, resulting in a reduction in the amount of byproducts formed. Particularly, in certain aspects, less than about 20%, less than about 15%, less than about 10%, less than about 8%, less than about 5%, less than about 3%, less than about 2%, or less than about 1% of an analogous $C_{(n-1)}$ alkane product is formed (e.g., such would be formed from the alcohol starting material via a reductive pathway). In other aspects, the amount of analogous $C_{(n-1)}$ internal olefins formed by the processes disclosed herein can be less than about 20%, less than about 15%, less than about 10%, less than about 8%, less than about 5%, less than about 3%, less than about 2%, or less than about 1%. Additionally or alternatively, the total amount of $C_{(n-1)}$ alkane and $C_{(n-1)}$ internal olefin byproducts produced from the processes disclosed herein can be less than about 20%, less than about 15%, less than about 10%, less than about 8%, less than about 5%, less than about 3%, less than about 2%, or less than about 1%. These percentages are molar yields based on the initial amount of the primary alcohol compound. Similarly, processes of the present invention in which the primary alcohol compound is a 1,2-diol can exhibit yields and byproducts in the same amounts and ranges described above.

While not wishing to be bound by theory, it is believed that the processes disclosed herein can be conducted as an equilibrium process subject to thermodynamic control, such that the amount and rate of the conversion of alcohol to olefin can be driven forward to the olefin product, or backward toward the primary alcohol compound. Given this understanding of the reaction mechanism, it will be apparent to one of skill in the art that the processes disclosed herein can be conducted as a continuous reaction in equilibrium, and that a rate of olefin formation can be controlled by removing at least a portion of the olefin from the reaction mixture, increasing the amount of the alcohol compound in the reaction mixture, increasing an amount of the catalyst composition in the reaction mixture, increasing an amount of the acceptor in the catalyst composition, increasing a reaction temperature of the contacting step, or any combination thereof.

For instance, in some aspects, a molar ratio of the primary alcohol compound to the Group VIII metal compound can be in a range from about 1:1000 to about 1:1, from about 1:500 to about 1:1, from about 1:200 to about 1:1, from about 1:200 to about 1:2, from about 1:200 to about 1:5, or from about 1:100 to about 1:10. In other aspects, the amount of the primary alcohol compound can be expressed as a ratio with the acceptor (alcohol:acceptor), and can be in a range from about 0.5:1 to about 1:20, from about 0.9:1 to about 1:10, or from about 1:1 to about 1:5, or from about 1:1 to about 1:3. In some aspects, these ratios can be fixed at the beginning of the reaction and change as the reaction progresses. Alternatively, the ratios of any reagents and products disclosed herein can be maintained as part of a continuous process as materials are consumed or removed (e.g., distilled) from the reaction mixture.

Moreover, in certain aspects, a reaction temperature of the contacting step and the formation of the olefin can be in a range from about 0° C. to about 300° C., from about 25° C. to about 250° C., from about 25° C. to about 200° C., from about 25° C. to about 175° C., from about 25° C. to about 150° C., from about 60° C. to about 200° C., from about 60° C. to about 175° C., or from about 60° C. to about 150° C., while not being limited thereto. Similarly, in certain aspects, a reaction time of the contacting step and the formation of the olefin often can be in a range from about 10 min to about 5 days, from about 10 min to about 3 days, from about 10 min to about 24 h, from about 1 h to about 12 h, or from about 1 h to about 3 h.

Oxidative Dehydroformylation Methods

Methods for the conversion of aldehydes to olefins are described herein. Generally, the oxidative dehydroformylation methods can comprise contacting any catalyst composition described herein with a substituted or unsubstituted $C_n$ aldehyde compound to form a reaction mixture comprising a substituted or unsubstituted $C_{(n-1)}$ olefin. In these methods, n can be an integer from 3 to 36. In some aspects, the catalyst composition can include an acceptor. The reaction below shows a representative example of an oxidative dehydroformylation method consistent with the present invention.

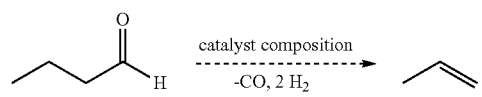

As would be recognized by those of skill in the art, the aldehyde compounds suitable for the oxidative dehydroformylation methods disclosed herein can be analogous to the primary alcohol compounds described above for the oxidative dehydroxymethylation processes. Thus, any features or structures of the primary alcohol compounds provided above also apply to the suitable aldehyde compounds, though substituting the primary alcohol functional group with an aldehyde functional group. Generally, suitable aldehyde compounds can include unsubstituted aldehyde compounds, substituted aldehyde compounds, substituted aldehyde compounds with protecting groups, linear aldehyde compounds, branched aldehyde compounds, saturated aldehyde compounds, unsaturated aldehyde compounds, cyclic aldehyde compounds, or any combination thereof. Similarly, for the conversion of an aldehyde to an olefin, the yields of $C_{(n-1)}$ olefins produced, the amounts of byproducts produced, and reaction conditions, can be the same as those disclosed above for the conversion of a primary alcohol to an olefin. The oxidative dehydroformylation methods disclosed herein also can be conducted under thermodynamic control, and operate continuously, as described above for the oxidative dehydroxymethylation processes.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Example 1

Reaction of 1-Dodecanol without an Acceptor

Example 1 was conducted by combining 1-dodecanol (0.2 mmol), [Rh(cod)OMe]2 (2 mol %), 3-OMeBzOH (4 mol %), and Xantphos (4 mol %) in 0.4 mL toluene and heating the solution to 90° C. (see reaction scheme below). The reaction continued for 24 h before analyzing the crude reaction mixture by gas chromatography using durene as an internal standard to determine the amount of 1-undecene, 1-undecane, and undecene isomers present in the reaction mixture. Gas chromatography analysis determined that only 1-undecane was present in the reaction mixture (10 mol % yield).

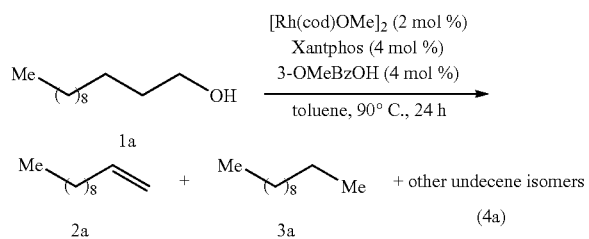

Examples 1A-1K

Reaction of 1-Dodecanol in the Presence of Various Acceptors

Examples 1A-1K utilized the general experimental procedure described above for Example 1, except that an acceptor (3 molar equivalents based on the primary alcohol) was used. Examples 1A-1K were conducted as single, individual experiments; results from each reaction are shown in Table 1 below. Surprisingly, Example 1K, which employed dimethylacrylamide as the acceptor, exhibited a dramatic and unexpected improvement to the selectivity of the reaction with respect to the $C_{(n-1)}$ olefin product, producing a 95% molar yield of the desired 1-undecene product, and only about 3 mol % of alkane and internal olefin byproducts. Moreover, Examples 1H-1J also demonstrated excellent selectivity, each having a yield of 1-undecene above 30%, using ethyl acrylate, t-butyl acrylate, and acrylamide, respectively.

TABLE 1

| Example | Acceptor | 1-undecene | 1-undecane | Isomers |
|---|---|---|---|---|
| 1A | norbornadiene | 32 | — | 2 |
| 1B | norbornene | 18 | — | 8 |
| 1C | acetone (Me-CO-Me) | — | 15 | — |
| 1D | cyclopentanone | — | 30 | — |
| 1E | Ph-CO-CF3 | — | 12 | — |
| 1F | methyl vinyl ketone | 10 | 7 | 2 |
| 1G | acrylonitrile (CH2=CH-CN) | 3 | 9 | — |
| 1H | ethyl acrylate (OEt) | 33 | 1 | 1 |
| 1I | t-butyl acrylate (OtBu) | 41 | 2 | 1 |
| 1J | acrylamide (NH2) | 35 | 2 | 1 |
| 1K | dimethylacrylamide (NMe2) | 95 | 1 | 2 |

Examples 2A-2T

Reaction of Various Primary Alcohol Compounds Using Dimethylacrylamide as the Acceptor Examples 2A-2T utilized the general experimental procedure described above for Inventive Example 1K (dimethylacrylamide), except that the primary alcohol compound reactant was substituted as indicated in the chart below; and except that 2H used 6 molar equivalents of dimethylacrylamide to account for the dual primary alcohol groups present in the starting material. The compounds shown below represent the primary alcohol compound and olefin product superimposed over the same structure; the dashed bonds represent the carbon-carbon bond broken during the reaction. Surprisingly, the oxidative dehydroxymethylation processes demonstrated a molar yield of the expected olefin in a range from 75% to 95%. Thus, the reaction is shown to be incredibly robust across compounds having protected groups (2L-2T) or additional functional groups comprising a π-bond present in the compound (2B-2G).

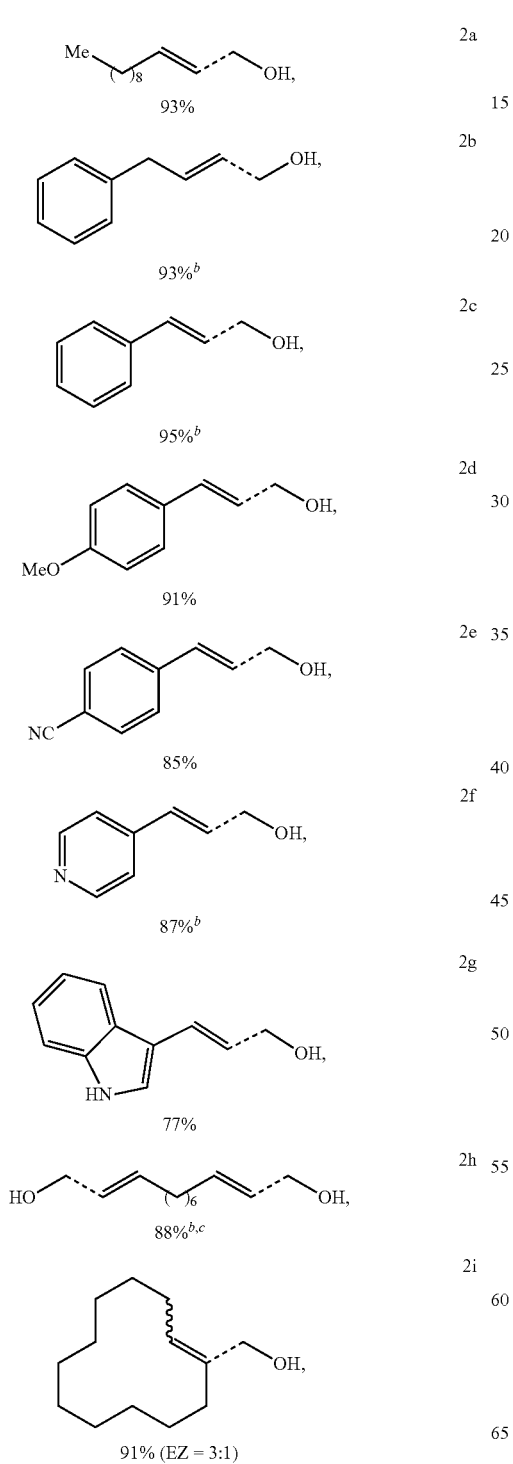

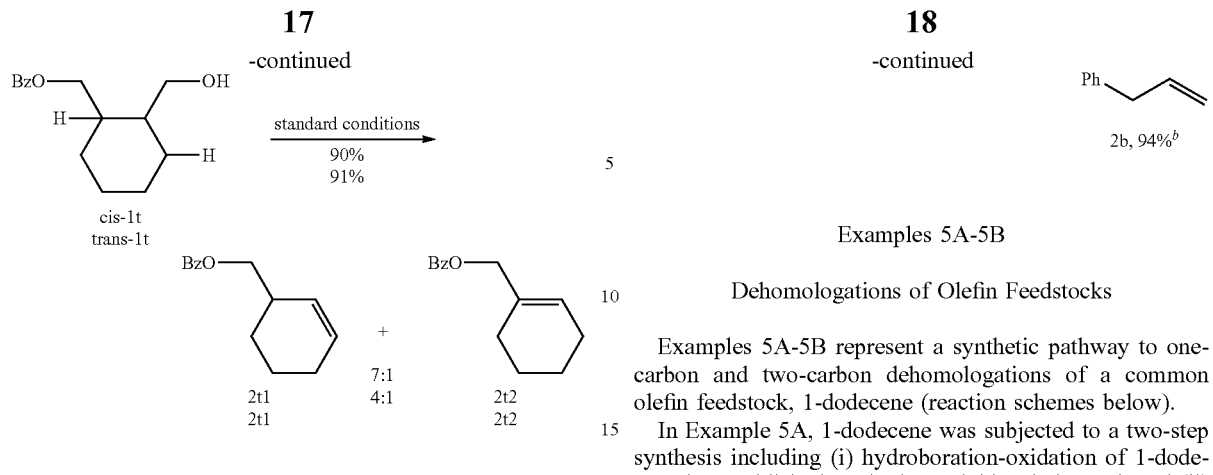

Examples 3A-3C

Reaction of Allylic Alcohols

Examples 3A-3C utilized the general experimental procedure described above for Inventive Example 1K (dimethylacrylamide), except that the primary alcohol compound reactant was substituted as indicated in the scheme below and only 1.5 equivalents of dimethylacrylamide were used. Surprisingly, the terminal olefin was produced in high yield, and without significant byproducts.

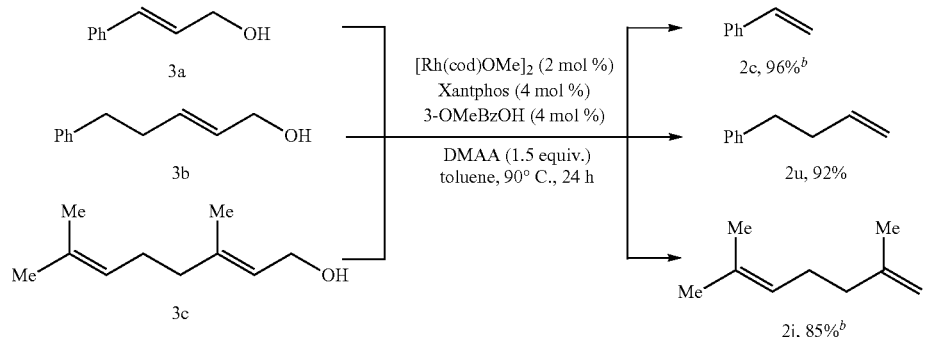
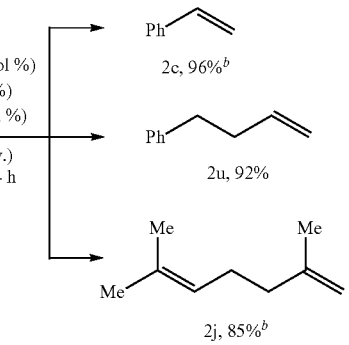

Example 4

Oxidative Dehydroformylation of an Aldehyde Compound

Example 4 utilized the general experimental procedure described above for Inventive Examples 3A-3C, except that the primary alcohol compound reactant was substituted for aldehyde compound 4, and the amount of [Rh(cod)OMe]2 (0.5 mol %), 3-OMeBzOH (1 mol %), and Xantphos (1 mol %) were reduced, and the reaction time was only 3 h. Surprisingly, the α-olefin product was formed in 94% yield in only 3 h, even though a comparatively small amount of the catalyst composition was used in the reaction.

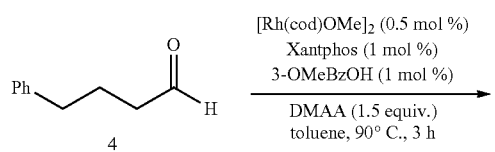

Examples 5A-5B

Dehomologations of Olefin Feedstocks

Examples 5A-5B represent a synthetic pathway to one-carbon and two-carbon dehomologations of a common olefin feedstock, 1-dodecene (reaction schemes below).

In Example 5A, 1-dodecene was subjected to a two-step synthesis including (i) hydroboration-oxidation of 1-dodecene by established methods to yield 1-dodecanol, and (ii) oxidative dehydroxymethylation of 1-dodecanol according to the general experimental procedure described above for Inventive Example 1K. The two-step process yielded the $C_{11}$ α-olefin in excellent yield (86%).

In Example 5B, 1-dodecene was subjected to a two-step process including (i) olefin dihydroxylation of 1-dodecene by established methods to yield 1,2-dodecanediol, and (ii) successive oxidative dehydroxymethylations of 1,2-dodecanediol according to the general experimental procedure described above for Inventive Example 1K, using twice the amount of sacrificial acceptor (4 molar equivalents) to account for the removal of an additional hydroxyl group (as in Example 2H). The two-step process yielded the Cm α-olefin in good yield (75%).

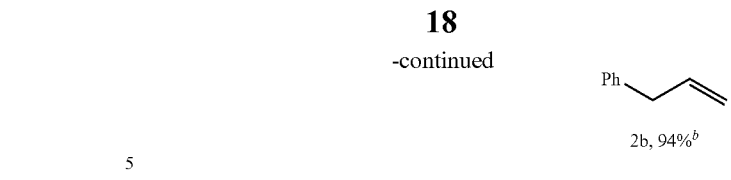
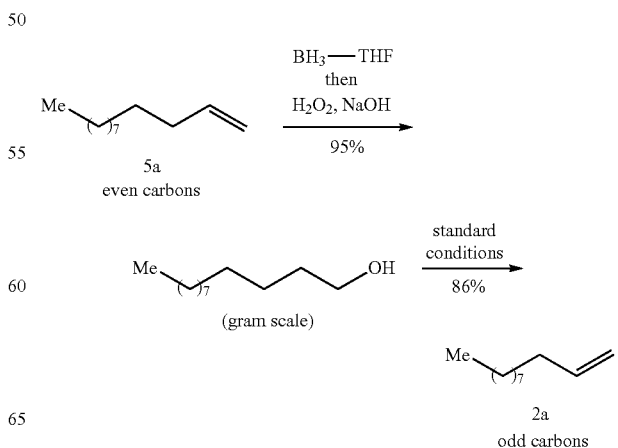

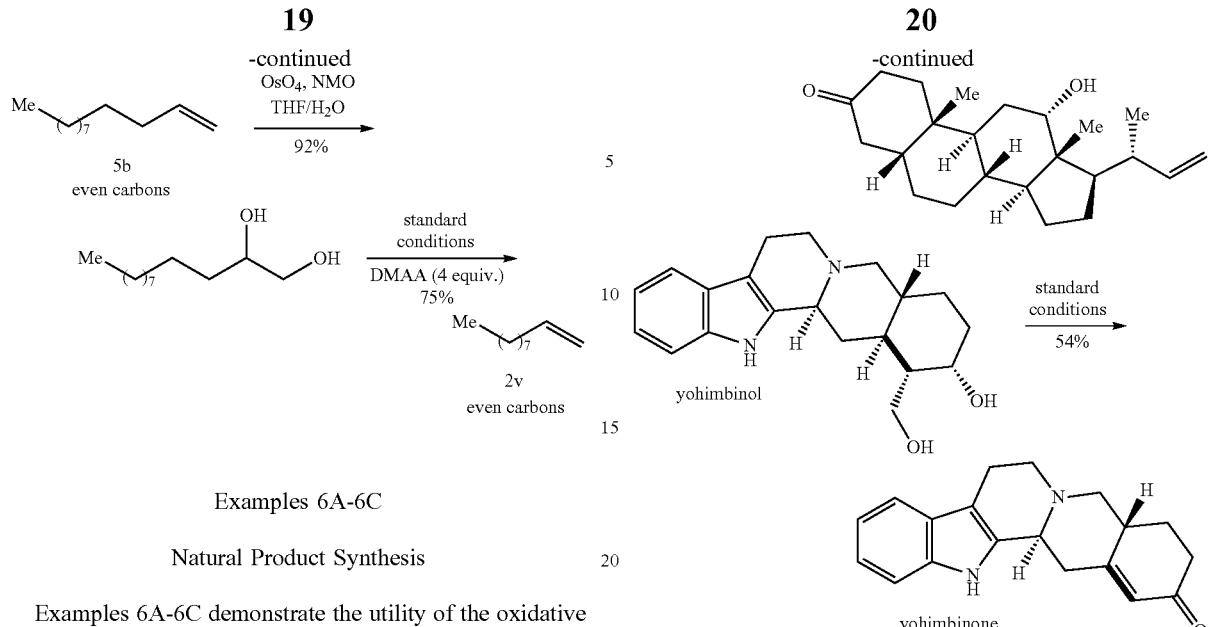

Examples 6A-6C

Natural Product Synthesis

Examples 6A-6C demonstrate the utility of the oxidative dehydroxymethylation processes disclosed herein for the synthesis of complex structures and in the presence of benzyl protecting groups or secondary hydroxyl groups. Each of Examples 6A-6C underwent oxidative dehydroxymethylation according to the general experimental procedure described above for Inventive Example 1K.

Example 6A provides an example of oxidative dehydroxymethylation performed in the presence of protected alcohol groups. Surprisingly, no debenzylation was observed, and the α-olefin product was formed in good yield.

Example 6B demonstrates oxidative dehydroxymethylation of a compound containing two unprotected secondary alcohol functional groups: one sterically accessible and one sterically hindered. Surprisingly, the sterically hindered secondary hydroxyl group was unaffected by the reaction. Further, the sterically accessible secondary hydroxyl group was converted to a ketone, and no further conversion of the ketone to an alkene was observed.

Example 6C takes advantage of the chemoselectivity demonstrated in Example 6B to provide a synthetic route to (+)-yohimbenone from yohimbenol in a single step. As shown below, the primary alcohol is converted to a Michael acceptor in good yield, despite the product being available as a potential sacrificial acceptor as the reaction progresses.

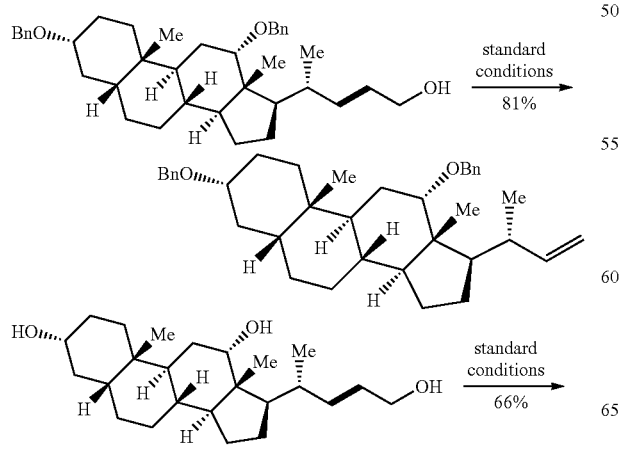

We claim:

1. A catalyst composition comprising:
   (i) a Group VIII metal compound;
   (ii) a heteroatomic ligand compound;
   (iii) a Bronsted acid compound; and
   (iv) an acceptor comprising an α,β-unsaturated ketone, an α,β-unsaturated amide, an α,β-unsaturated thioester, or any combination thereof.

2. The catalyst composition of claim 1, wherein:
   the metal compound comprises a rhodium compound, a cobalt compound, an iridium compound, or a combination thereof;
   the heteroatomic ligand compound comprises a phosphine donor group, an amine donor group, a sulfide donor group, or any combination thereof; and
   the Bronsted acid compound is a carboxylic acid.

3. The catalyst composition of claim 1, wherein:
   the metal compound is [Rh(cod)OMe]$_2$;
   the heteroatomic ligand compound is Xantphos; and
   the Bronsted acid compound is 3-methoxybenzoic acid.

4. The catalyst composition of claim 1, wherein:
   a molar ratio of the metal compound to the heteroatomic ligand compound is in a range from about 5:1 to about 1:5;
   a molar ratio of the heteroatomic ligand compound to the Bronsted acid compound is in a range from about 5:1 to about 1:5; and
   a molar ratio of the metal compound to the acceptor is in a range from about 1:1000 to about 1:1.

5. An oxidative dehydroxymethylation process, the process comprising:
   contacting the catalyst composition of claim 1 with a substituted or unsubstituted $C_n$ primary alcohol compound to form a reaction mixture comprising a substituted or unsubstituted $C_{(n-1)}$ olefin;
   wherein n is an integer from 3 to 36.

6. The process of claim 5, wherein a molar ratio of the primary alcohol compound to the metal compound is in a range from about 1000:1 to about 10:1.

7. The process of claim 5, wherein a yield of the olefin is at least about 20 mol %.

8. The process of claim 5, wherein:
n is an integer from 3 to 18;
a yield of the olefin is at least about 60 mol %; and
the reaction mixture comprises less than 10 mol % $C_{(n-1)}$ and/or $C_{(n-2)}$ alkanes.

9. The process of claim 8, wherein a yield of the olefin is at least about 90 mol %.

10. The process of claim 5, wherein the olefin is an α-olefin.

11. The process of claim 5, wherein:
the contacting step is conducted in the presence of a hydrophobic solvent; and
a reaction temperature of the contacting step is in a range from about 0 to about 300° C.

12. An oxidative dehydroxymethylation process, the process comprising:
contacting the catalyst composition of claim 1 with a substituted or unsubstituted $C_n$ primary alcohol compound to form a reaction mixture comprising a substituted or unsubstituted $C_{(n-2)}$ olefin; wherein:
n is an integer from 4 to 36; and
the primary alcohol compound is a 1,2-diol.

13. The process of claim 12, wherein:
a yield of the olefin is at least about 20 mol %; and
the reaction mixture comprises less than 10 mol % $C_{(n-1)}$ and/or $C_{(n-2)}$ alkanes.

14. The process of claim 12, wherein a molar ratio of the primary alcohol compound to the metal compound is in a range from about 1000:1 to about 10:1.

15. An oxidative dehydroformylation method, the method comprising:
contacting the catalyst composition of claim 1 with a substituted or unsubstituted $C_n$ aldehyde compound to form a reaction mixture comprising a substituted or unsubstituted $C_{(n-1)}$ olefin;
wherein n is an integer from 3 to 36.

16. The method of claim 15, wherein:
the contacting step is conducted in the presence of a hydrophobic solvent; and
a reaction temperature of the contacting step is in a range from about 0 to about 300° C.

17. A catalyst composition comprising:
(i) a Group VIII metal compound;
(ii) a heteroatomic ligand compound;
(iii) a Bronsted acid compound; and
(iv) an acceptor comprising methyl vinyl ketone, acrylonitrile, ethyl acrylate, t-butyl acrylate, acrylamide, dimethylacrylamide, or any combination thereof.

18. The catalyst composition of claim 17, wherein:
the metal compound comprises a rhodium compound, a cobalt compound, an iridium compound, or a combination thereof;
the heteroatomic ligand compound comprises a phosphine donor group, an amine donor group, a sulfide donor group, or any combination thereof; and
the Bronsted acid compound is a carboxylic acid.

19. The catalyst composition of claim 18, wherein:
a molar ratio of the metal compound to the heteroatomic ligand compound is in a range from about 5:1 to about 1:5;
a molar ratio of the heteroatomic ligand compound to the Bronsted acid compound is in a range from about 5:1 to about 1:5; and
a molar ratio of the metal compound to the acceptor is in a range from about 1:1000 to about 1:1.

20. The catalyst composition of claim 17, wherein:
the metal compound is $[Rh(cod)OMe]_2$;
the heteroatomic ligand compound is Xantphos; and
the Bronsted acid compound is 3-methoxybenzoic acid.

21. An oxidative dehydroxymethylation process, the process comprising:
contacting the catalyst composition of claim 17 with a substituted or unsubstituted $C_n$ primary alcohol compound to form a reaction mixture comprising a substituted or unsubstituted $C_{(n-1)}$ olefin;
wherein n is an integer from 3 to 36.

22. An oxidative dehydroxymethylation process, the process comprising:
contacting the catalyst composition of claim 17 with a substituted or unsubstituted $C_n$ primary alcohol compound to form a reaction mixture comprising a substituted or unsubstituted $C_{(n-2)}$ olefin; wherein:
n is an integer from 4 to 36; and
the primary alcohol compound is a 1,2-diol.

23. An oxidative dehydroformylation method, the method comprising:
contacting the catalyst composition of claim 17 with a substituted or unsubstituted $C_n$ aldehyde compound to form a reaction mixture comprising a substituted or unsubstituted $C_{(n-1)}$ olefin;
wherein n is an integer from 3 to 36.

24. A catalyst composition comprising:
(i) a Group VIII metal compound;
(ii) a heteroatomic ligand compound;
(iii) a Bronsted acid compound; and
(iv) an acceptor comprising dimethylacrylamide.

25. The catalyst composition of claim 24, wherein:
the metal compound comprises a rhodium compound, a cobalt compound, an iridium compound, or a combination thereof;
the heteroatomic ligand compound comprises a phosphine donor group, an amine donor group, a sulfide donor group, or any combination thereof; and
the Bronsted acid compound is a carboxylic acid.

26. The catalyst composition of claim 25, wherein:
a molar ratio of the metal compound to the heteroatomic ligand compound is in a range from about 5:1 to about 1:5;
a molar ratio of the heteroatomic ligand compound to the Bronsted acid compound is in a range from about 5:1 to about 1:5; and
a molar ratio of the metal compound to the acceptor is in a range from about 1:1000 to about 1:1.

27. The catalyst composition of claim 24, wherein:
the metal compound is $[Rh(cod)OMe]_2$;
the heteroatomic ligand compound is Xantphos; and
the Bronsted acid compound is 3-methoxybenzoic acid.

* * * * *